US012773273B2

(12) United States Patent
Wang et al.

(10) Patent No.: US 12,773,273 B2
(45) Date of Patent: Oct. 27, 2026

(54) MEDICAL CATHETER AND THREE-DIMENSIONAL MAGNETIC POSITIONING SYSTEM

(71) Applicant: SHANGHAI MICROPORT EP MEDTECH CO., LTD., Shanghai (CN)

(72) Inventors: Hui Wang, Shanghai (CN); Ziyan Zhou, Shanghai (CN); Jingjing Gong, Shanghai (CN); Lei Shen, Shanghai (CN); Yiyong Sun, Shanghai (CN); Bo Liang, Shanghai (CN)

(73) Assignee: SHANGHAI MICROPORT EPMEDTECHCO., LTD., Shanghai (CN)

( * ) Notice: Subject to any disclaimer, the term of this patent is extended or adjusted under 35 U.S.C. 154(b) by 357 days.

(21) Appl. No.: 18/551,799

(22) PCT Filed: Mar. 21, 2022

(86) PCT No.: PCT/CN2022/082096
§ 371 (c)(1),
(2) Date: Sep. 21, 2023

(87) PCT Pub. No.: WO2022/218108
PCT Pub. Date: Oct. 20, 2022

(65) Prior Publication Data

US 2024/0180632 A1 Jun. 6, 2024

(30) Foreign Application Priority Data

Apr. 15, 2021 (CN) ......................... 202110407610.3

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/25* (2016.02); *A61B 90/06* (2016.02);
(Continued)

(58) Field of Classification Search
CPC .......... A61M 25/0127; A61M 25/0068; A61B 34/20
See application file for complete search history.

(56) References Cited

U.S. PATENT DOCUMENTS

2008/0171934 A1* 7/2008 Greenan .................. A61B 5/06
606/108
2018/0289356 A1* 10/2018 Buesseler ......... A61M 25/0136
(Continued)

FOREIGN PATENT DOCUMENTS

CN 111001075 A 4/2020
CN 111012450 A 4/2020
(Continued)

*Primary Examiner* — Anne M Kozak
*Assistant Examiner* — Kaitlyn Eunji Kim
(74) *Attorney, Agent, or Firm* — MUNCY, GEISSLER, OLDS & LOWE, P.C.

(57) ABSTRACT

A medical catheter and a three-dimensional magnetic positioning system. The medical catheter includes a catheter body, a first magnetic sensor and a second magnetic sensor. The catheter body includes, sequentially connected along an axis thereof, a tip section, a bending-adjustable section and a straight section. Both the first magnetic sensor and the second magnetic sensor are disposed on the tip section. This medical catheter can be more accurately located and controlled.

11 Claims, 6 Drawing Sheets

(51) Int. Cl.
*A61B 90/00* (2016.01)
*A61M 25/00* (2006.01)
*A61M 25/01* (2006.01)

(52) U.S. Cl.
CPC . *A61B 2034/2051* (2016.02); *A61B 2090/064* (2016.02); *A61M 25/0068* (2013.01); *A61M 25/0082* (2013.01); *A61M 25/0127* (2013.01); *A61M 2205/0216* (2013.01); *A61M 2205/3327* (2013.01)

(56) References Cited

U.S. PATENT DOCUMENTS

| | | | | |
|---|---|---|---|---|
| 2019/0388156 | A1* | 12/2019 | Shameli ................. | A61B 34/20 |
| 2020/0188635 | A1 | 6/2020 | Barrish et al. | |

FOREIGN PATENT DOCUMENTS

| | | | | |
|---|---|---|---|---|
| CN | 111068162 A | 4/2020 | | |
| CN | 111743629 A | 10/2020 | | |
| CN | 111001075 B * | 1/2022 | ........ | A61M 25/0127 |
| CN | 215653333 U | 1/2022 | | |
| EP | 0776176 B1 | 12/1999 | | |
| RU | 2563384 C1 | 9/2015 | | |
| RU | 2630621 C2 | 9/2017 | | |
| RU | 2676841 C2 | 1/2019 | | |
| WO | WO-2012/150567 A1 | 11/2012 | | |

* cited by examiner

MEDICAL CATHETER AND THREE-DIMENSIONAL MAGNETIC POSITIONING SYSTEM

TECHNICAL FIELD

The present invention relates to the field of medical devices and, in particular, to a medical catheter and a three-dimensional (3D) magnetic positioning system.

BACKGROUND

Cardiovascular disease is a serious threat to human health due to its high prevalence, disability and mortality. At present, minimally invasive interventional surgery has been recognized as a relatively effective approach for clinical diagnosis and treatment of cardiovascular disease. Minimally invasive interventional surgery involves the use of medical catheters of various structures, shapes and sizes. In the design and fabrication of medical catheters, depending on their expected uses, they are pre-bent distally into different shapes which adapt to the anatomical shapes of particular lesions and facilitate their conformance therewith. In recent years, many medical catheters of various shapes and preformed distal angles have been developed and put into clinical use. However, for individuals with atypical anatomies, even medical catheters made with preformed distal shapes specially designed for particular anatomies may not go well with the patients' unique anatomies, and one or more attempts with other medical catheters having different preformed shapes would be frequently necessary during the surgical procedures. This may increase the patients' surgical burden. Therefore, in recent years, medical catheters with adjustable distal bending have been developed, which allows repeated in vitro adjustment of their distal bent angles for adaptation to various anatomical shapes.

Conventional electrophysiological intervention is carried out in a two-dimensional (2D) mode, in which a medical professional advances a distal end of a medical catheter to a lesion site in a patient under the guidance of X-ray imaging machine following the manufacturer's instructions. This operation is, however, time-consuming, insufficiently accurate and risky. Even a surgeon with rich experience in electrophysiological intervention would require repeated X-ray imaging to determine the heart's shape and hence the location of the medical catheter. This can lead to significant radiation exposure of both the patients and the surgeon.

In order to overcome this, there have been developed medical catheters with tactile sensing and magnetic locating capabilities and adjustable bending, which can sense information about a contact force between the catheter's distal end and tissue and about a pose of the distal end, calculate a vector of the contact force based on the information and determine a particular anatomy from the vector. For example, during passage of the distal end of the medical catheter through an ostium of a pulmonary vein, the direction of the contact force vector will experience a jump, based on which, a surgeon can know that the distal end of the medical catheter is current located at an ostium of a pulmonary vein. A medical catheter with magnetic locating capacities may be used in combination with a 3D positioning device which can estimate the location of tissue that the catheter's distal end is contacting on an electroanatomical map from a signal indicating the position of the distal end and a contact force vector and thereby update the electroanatomical map. The 3D positioning device can also calculate a bending direction based on information about the contact force between the distal end of the medical catheter and tissue and about a pose of the distal end, which can provide guidance to a surgeon and enables his/her precise control over the medical catheter such that the distal end of the medical catheter can be fitted with target tissue. Moreover, how well the distal end is fitted with the tissue may be assessed without using X-rays, reducing radiation exposure of both the surgeon and the patient and resulting in improved surgical safety. However, existing medical catheters of this type are associated with the problem of suboptimal locating accuracy due to insensible positioning of magnetic sensors.

SUMMARY OF THE INVENTION

It is an object of the present invention to provide a medical catheter and a three-dimensional (3D) magnetic positioning system, which seeks to enable more accurate control over the medical catheter by precisely locating a tip section of the medical catheter using magnetic sensors and displaying its pose, allowing an interventional procedure using the catheter to be conducted in a more accurate way. Moreover, radiation exposure of both a surgeon and a patient can be avoided, resulting in higher surgical safety.

To this end, the present invention provides a medical catheter comprising a catheter body, a first magnetic sensor and a second magnetic sensor, the catheter body comprising, sequentially connected along an axis thereof, a tip section, a bending-adjustable section and a straight section, both the first and second magnetic sensors disposed on the tip section.

Optionally, the first and second magnetic sensors may be oriented at an angle with respect to each other.

Optionally, the angle oriented between the first and second magnetic sensors may range from 5° to 175°.

Optionally, the tip section may comprise a structural member having a proximal end connected to the bending-adjustable section, wherein the first magnetic sensor is disposed on the structural member.

Optionally, the structural member may define a first channel whose axis is at an angle with an axis of the structural member, wherein the first magnetic sensor is at least partially disposed in the first channel.

Optionally, the second magnetic sensor may be disposed on the structural member.

Optionally, the structural member further may define a second channel, which is spaced apart from the first channel circumferentially around the structural member and has an axis that is at an angle with the axis of the first channel, wherein the second magnetic sensor is at least partially disposed in the second channel.

Optionally, the axis of the second channel may be configured to be parallel to the axis of the structural member.

Optionally, the structural member may be configured to be ferromagnetic, wherein the second magnetic sensor comprises an inductive coil at least partially wound on an outer circumferential surface of the structural member.

Alternatively, the structural member may comprise a non-ferromagnetic body and a ferromagnetic core tube disposed over the body, wherein the first channel is defined in the body and the second magnetic sensor comprises an inductive coil at least partially winding on an outer circumferential surface of the structural member.

Optionally, the angle between the axis of the first channel and the axis of the structural member may range from 5° to 10°.

Optionally, the structural member may define one said first channel and three second channels, which are circumferentially spaced apart from one another, wherein at least one of the second channels is in an angle with the first channel, and in a radial cross-section of the structural member, each of the second channels has an at least partially open contour.

Optionally, the second channels may be configured for accommodating therein the second magnetic sensor, or for passing therethrough the second magnetic sensor and lead thereof, or for flowing therethrough a medium, wherein on a circumference of the structural member, one of the three second channels opposes the first channel, and the remaining two second channels are located on opposing sides of the first channel, and wherein in the radial cross-section of the structural member, the contour of each of the second channels comprises an arc edge and two straight edges extending from respective ends of the arc edge.

Optionally, the straight edges of the second channel that opposes the first channel may be parallel to a line connecting a center of the first channel and a center of the arc edge of the specific second channel in opposition to the first channel, wherein the straight edges of one of the remaining two second channels are perpendicular to the line, and wherein the straight edges of the other are inclined relative to the line, and a distance from a center of the arc edge of the other to the center of the arc edge of the second channel in opposition to the first channel is smaller than a distance from the center of the arc edge of the other to the center of the first channel.

Optionally, the tip section may comprise a tip electrode which is disposed at a distal end of the tip section, the tip electrode defining a third channel, wherein the second magnetic sensor is at least partially disposed in the third channel.

Optionally, the first and second magnetic sensors may be staggered from one another, both circumferentially around and axially along the tip section.

Optionally, an axis of the third channel may be parallel to an axis of the tip electrode.

Optionally, the tip section may further comprise an elastomer provided thereon with a strain sensor, the strain sensor configured for sensing the magnitude of an external force that the tip section is subject to when it is deforming.

Optionally, the medical catheter may further comprise a third magnetic sensor and a fourth magnetic sensor, which are disposed within the straight section at a distal end thereof and are oriented at an angle with respect to each other.

Optionally, the first, second, third and fourth magnetic sensors may all be five-degree-of-freedom (5DoF) sensors.

To the above end, the present invention also provides a 3D magnetic positioning system comprising a positioning device and the medical catheter as defined above.

The positioning device comprises a position processing unit and a display unit. The position processing unit is communicatively connected to both the first and second magnetic sensors.

The position processing unit is configured to acquire pose information of both the first and second magnetic sensors and derive pose information of the tip section from the pose information of the first and second magnetic sensors.

The display unit is communicatively connected to the position processing unit and configured to receive and display the pose information of the tip section.

Optionally, when the medical catheter further comprises the third and fourth magnetic sensors, the third and fourth magnetic sensors may be disposed in the straight section at the distal end thereof and both communicatively connected to the position processing unit, wherein the position processing unit is further configured to acquire pose information of the third and fourth magnetic sensors and derive pose information of the distal end of the straight section from the pose information of the third and fourth magnetic sensors, as well as pose information of the bending-adjustable section from the pose information of both the tip section and the distal end of the straight section, and the display unit is configured to receive and display the pose information of the bending-adjustable section.

Optionally, the position processing unit may be configured to visualize the pose information of the tip section and the pose information of the bending-adjustable section, wherein the display unit is configured to receive and display the visualized pose information. Alternatively or additionally, the position processing unit may also be configured to derive an expected bending direction for the bending-adjustable section from the pose information of the tip section.

Optionally, the medical catheter may further comprise a strain sensor, which is disposed on the tip section, configured to sense the magnitude of an external force acting on, and causing deformation of, the tip section, and communicatively connected to the position processing unit, wherein the position processing unit is further configured to derive a force vector on the tip section from the pose information of the tip section and the magnitude of the external force on the tip section, and the display unit is configured to receive and display the force vector.

Compared with the prior art, the medical catheter and 3D magnetic positioning system of the present invention have the advantages as follows:

The medical catheter includes the catheter body, the first magnetic sensor and the second magnetic sensor. The catheter body includes, sequentially joined along the axis thereof, a tip section, the bending-adjustable section and the straight section. Both the first and second magnetic sensors are disposed on the tip section. In an interventional procedure, the medical catheter can be used in combination with the positioning device which can locate the tip section of the medical catheter in a patient's body. Moreover, under the guidance of an image, an operator can precisely control bending of the bending-adjustable section, enabling the distal end of the medical catheter to reach a target site and preventing both the operator and the patient from radiation exposure. As both magnetic sensors are provided on the tip section, it is possible to more accurately determine the pose of the tip section, and the two magnetic sensors will not be affected at all during bending adjustment of the medical catheter. This lowers the risk of breakage of the magnetic sensors and ensures magnetic locating reliability.

BRIEF DESCRIPTION OF THE DRAWINGS

The accompanying drawings are provided to facilitate a better understanding of the present invention and do not unduly limit the scope thereof in any sense, in which.

DETAILED DESCRIPTION

Figure 1:
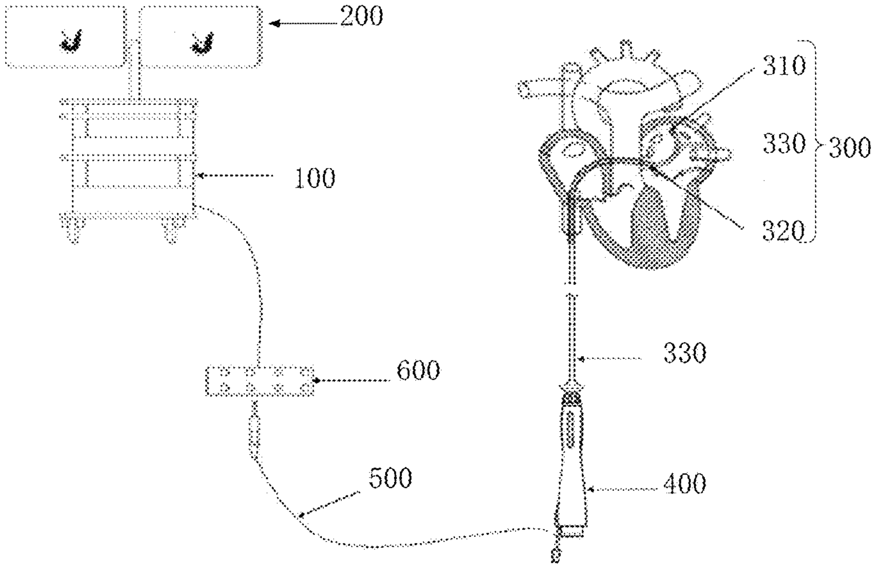
FIG. 1 schematically illustrates an application scenario of a three-dimensional (3D) magnetic positioning system according to an embodiment of the present invention.

Particular embodiments of the present invention will be described below by way of specific examples. Based on the disclosure and teachings provided herein, a person of ordinary skill in the art will readily realize other advantages and benefits provided by the present invention. The present invention may also be otherwise embodied or applied through different embodiments, and various modifications or changes may be made to the details disclosed herein from different points of view or for different applications, without departing from the spirit of the present invention. It should be noted that the accompanying drawings are provided herein merely to schematically illustrate the basic concept of the present invention. Accordingly, they only show components relating to the present invention but not necessarily depict all the components as well as their real shapes and dimensions in practical implementations. In practice, the configurations, counts and relative scales of the components may vary arbitrarily and their arrangements may be more complicated.

In the following, each of the embodiments is described as having one or more technical features. However, this does not mean that the present invention must be practiced necessarily with all such technical features, or separately with some or all the technical features in any of the embodiments. In other words, as long as the present invention can be put into practice, a person skilled in the art may choose some or all of the technical features in any of the embodiments or combine some or all of the technical features in different embodiments based on the teachings herein and depending on relevant design specifications or the requirements of practical applications. In this way, the present invention can be carried out more flexibly.

As used herein, the singular forms “a”, “an” and “the” include plural referents, and the plural form “a plurality of” means “two or more”, unless the context clearly dictates otherwise. As used herein, the term “or” is generally employed in the sense including “and/or”, unless the context clearly dictates otherwise. The terms “mounting”, “coupling” and “connection” should be interpreted in a broad sense. For example, a connection may be a permanent, detachable or integral connection, or a mechanical or electrical connection, or a direct or indirect connection with one or more intervening media, or an internal communication or interaction between two elements. Those of ordinary skill in the art can understand the specific meanings of the above-mentioned terms herein, depending on their context. The term “proximal end” generally refers to an end closer to an operator, and the term “distal end” generally refers to an end closer to a patient (i.e., the end that enters the patient’s body first to access a lesion therein).

In principle, the present invention provides a three-dimensional (3D) magnetic positioning system including a positioning device and a medical catheter. The positioning device includes a position processing unit and a display unit. The medical catheter incudes a catheter body, a first magnetic sensor and a second magnetic sensor. The catheter body includes a tip section, a bending-adjustable section and a straight section, which are sequentially joined along an axis of the catheter body. Both the first and second magnetic sensors are provided on the tip section and communicatively connected to the position processing unit. The position processing unit is configured to acquire pose information of both the first and second magnetic sensors and derive pose information of the tip section from the pose information of the first and second magnetic sensors. The display unit is communicatively connected to the position processing unit and configured to receive and display the pose information of the tip section. More preferably, the position processing unit can visualize the pose information of the tip section, and the display unit receives and displays the visualized pose information. The present invention is not limited to any particular approach for visualizing the pose information by the position processing unit. It will be recognized that the pose information includes spatial position information and orientation information. The medical catheter may be a guide sheath or an electrophysiological catheter. The electrophysiological catheter may be a radio-frequency (RF) ablation catheter or a mapping catheter.

When the 3D magnetic positioning system is used to perform an interventional procedure, the position and orientation of the tip section of the medical catheter in the body of a patient may be tracked in real time with the first and second magnetic sensors and displayed on the display unit at the same time. This enables more accurate control of the medical catheter. For example, when the medical catheter is a guide sheath, this can facilitate fast establishment of a guide path within the patient’s body, or when the medical catheter is an electrophysiological catheter, this can facilitate advancement of a distal end of the medical catheter to a target site. In addition, radiation exposure of the patient and a surgeon could be avoided, resulting in higher safety of the interventional procedure. In particular, through disposing both the magnetic sensors on the tip section of the medical catheter, more accurate pose information of the tip section can be acquired. Apart from this, placing the magnetic sensors on the tip section avoids them from being stressed and possibly broken during bending adjustment of the bending-adjustable section, ensuring magnetic locating reliability.

Objects, advantages and features of the present invention will become more apparent upon reading the following more detailed description of the present invention, which is made with reference to the accompanying drawings. Note that the figures are provided in a very simplified form not necessarily drawn to exact scale and for the only purpose of facilitating easy and clear description of the embodiments. Throughout the several views, like numerals indicate like elements.

Figure 2:
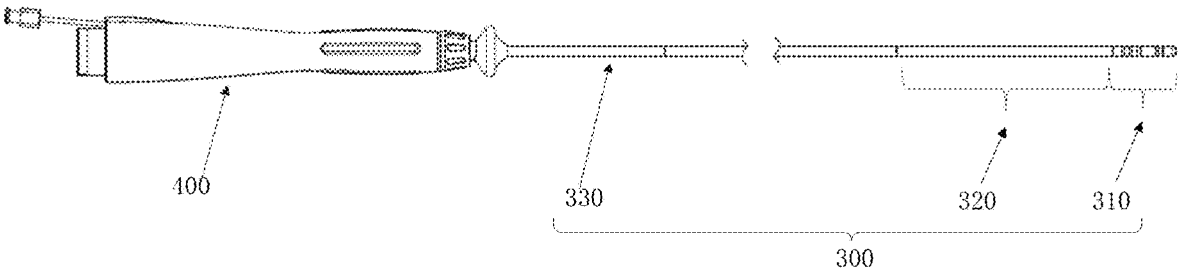
FIG. 2 is a schematic diagram showing the structure of a medical catheter according to a first embodiment of the present invention.

As shown in FIG. 1, embodiments of the present invention relate to a three-dimensional (3D) magnetic positioning system including a medical catheter and a positioning device. The positioning device includes a position processing unit 100 and a display unit 200. With additional reference to FIG. 2, the medical catheter includes a catheter body 300 and a control handle 400 coupled to the catheter body 300. The catheter body 300 includes tip section 310, a bending-adjustable section 320 and a straight section 330, which are sequentially joined along an axis of the catheter body 300. The straight section 330 has a proximal end connected to the control handle 400 which is configured to control bending of the bending-adjustable section 320. The medical catheter may be a guide sheath, or a mapping or ablation catheter.

Figure 3:
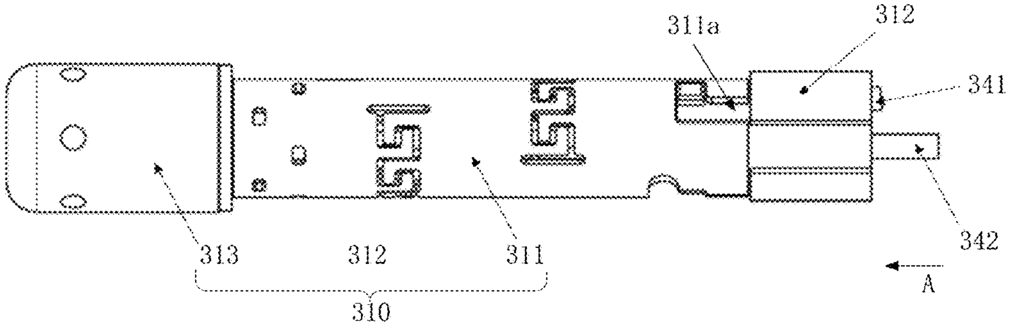
FIG. 3 is a schematic diagram showing the structure of a tip section of the medical catheter in the first embodiment of the present invention.
Figure 4:
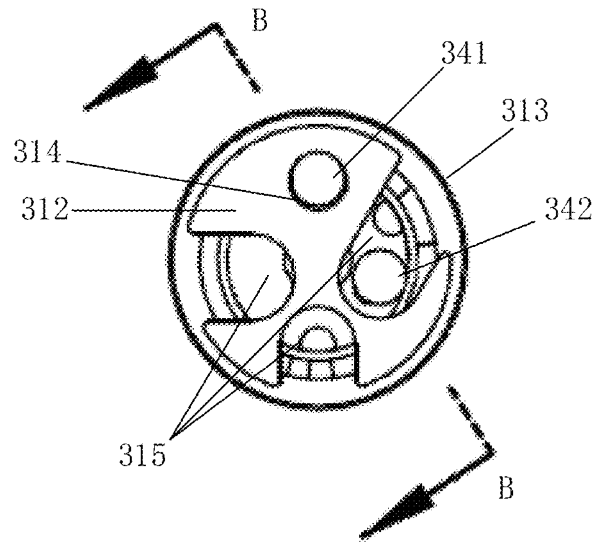
FIG. 4 is a schematic illustration of the tip section of the medical catheter of FIG. 3 as viewed in direction A.

As shown in FIGS. 3 and 4, the medical catheter further includes a first magnetic positioning mechanism for acquiring pose information of the tip section 310. It will be recognized that the pose information includes spatial position information and orientation information. The first magnetic positioning mechanism is provided on the tip section 310. This is advantageous in that the pose of the tip section 310 can be more accurately determined and that the first magnetic positioning mechanism will not be adversely affected during bending adjustment of the bending-adjustable section 320 (for example, it may be stressed and possibly broken and lose its magnetic locating function).

According to embodiments of the present invention, the first magnetic positioning mechanism includes a first magnetic sensor 341 and a second magnetic sensor 342. Preferably, referring to FIG. 5, the first and second magnetic sensors 341, 342 are oriented on the tip section 310 at an angle with respect to each other in a range of 5°-175° (including 5° and 175°), with 90° being preferred. It will be appreciated that the angle between the two magnetic sensors refers to angle formed by axes of the two magnetic sensors when the tip section 310 assumes a linear shape.

When used in an interventional procedure, both the first and second magnetic sensors 341, 342 are communicatively connected to the position processing unit 100, for example, by a lead 500 and a connector 600. The position processing unit 100 is configured to acquire pose information of the first and second magnetic sensors 341, 342 and derive pose information of the tip section 310 from the pose information of the first and second magnetic sensors 341, 342. The display unit 200 is configured to receive and display the pose information of the tip section 310, allowing an operator to be aware of the current pose of the tip section 310 in real time.

The position processing unit 100 is also configured to determine an expected bending direction for the bending-adjustable section 320 based on the pose information of the tip section 310. The display unit 200 is configured to receive and display the expected bending direction for the bending-adjustable section 320, and the operator may then manipulate the control handle 400 to bend the bending-adjustable section 320 in the expected bending direction. This can improve control accuracy of the medical catheter.

Optionally, both the first and second magnetic sensors 341, 342 are 5-degree-of-freedom (5DoF) sensors, which may be synthesized into a 6DoF sensor. That is, this is equivalent to tracking the pose of the tip section 310 with a single 6DoF sensor. In this way, good locating performance can be achieved, and compared with using a "real" 6DoF sensor, the synthesized one is less bulky and inexpensive, allowing the medical catheter to have a reduced size and manufactured at lower cost.

Depending on the configuration of the medical catheter, the position processing unit 100 may synthesize pose information of a single 6DoF sensor from the pose information of the first and second magnetic sensors 341, 342 and derive the pose information of the tip section 310 from the pose information of the 6DoF sensor. According to the present invention, the two 5DoF sensors may be synthesized into the 6DoF sensor using a known prior technique, and detailed description thereof is omitted herein.

It will be appreciated that the synthesized 6DoF sensor can rotate and move freely in the space, and its location, rotation and movement correspond to those of the tip section 310. In this way, the position and orientation of the tip section 310 can be accurately determined using the 6DoF sensor, resulting in improved locating accuracy of the medical catheter, which is helpful in enhancing control accuracy of the medical catheter and facilitates fast and accurate advancement of a distal end of the medical catheter to a lesion site.

The orientation information of the tip section 310 is primarily use for the derivation of its angle information, i.e., angle information of the 6DoF sensor. In generally, it may be represented with a rotation matrix, a rotation vector, a quaternion or Euler angles, and these alternative representations may be converted to one another. It is a common practice to use Euler angles for this purpose. In some embodiments, the orientation information of the tip section 310 may be represented by a rotation matrix. For example, assume a known quaternion $q=(\theta\ x\ y\ z)^T$ in a Cartesian coordinate system xyz, where θ is an angle of rotation, (x y z) is a unit vector, x is a coordinate on the x axis, y is a coordinate on the y axis and z is a coordinate on the z axis, when the unit vector ω=(xyz) is rotated by an angle of θ, the rotation matrix R can be obtained according to the quaternion, as:

$$R=\begin{bmatrix}\cos\theta+x^2(1-\cos\theta) & -z\sin\theta+xy(1-\cos\theta) & y\sin\theta+xz(1-\cos\theta)\\ z\sin\theta+xy(1-\cos\theta) & \cos\theta+y^2(1-\cos\theta) & -x\sin\theta+yz(1-\cos\theta)\\ -y\sin\theta+xz(1-\cos\theta) & x\sin\theta+yz(1-\cos\theta) & \cos\theta+z^2(1-\cos\theta)\end{bmatrix} \quad (1\text{-}1)$$

Figure 6:
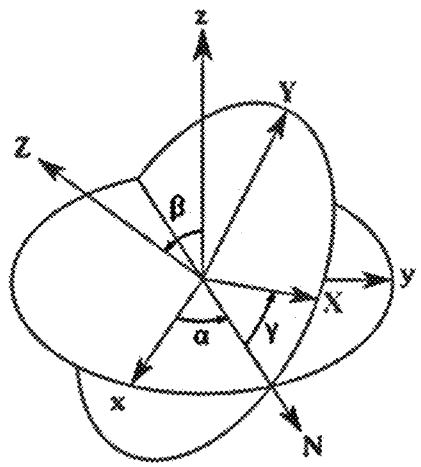
FIG. 6 is a diagram showing a coordinate transformation for rotation of a 6DoF sensor in the first embodiment of the present invention.

This rotation matrix R can be represented by Euler angles denoting angles of rotation about the respective axes of the coordinate system. Euler angles are used to describe a sequence of intrinsic rotations required to reach a new reference frame, starting from a fixed reference frame whose orientation is known. FIG. 6 shows an original reference frame xyz with axes denoted as x, y, z and a new reference frame XYZ with axes denoted as X, Y, Z obtained by rotating the original reference frame. In the figure, N denotes the so-called line of nodes, which is the intersection of the planes xy and XY.

In case of Euler angles being used to represent the pose of the tip section 310, it may be first described with the following matrix:

$$R=\begin{bmatrix}1&0&0\\0&\cos\alpha&-\sin\alpha\\0&\sin\alpha&\cos\alpha\end{bmatrix}\begin{bmatrix}\cos\beta&0&\sin\beta\\0&1&0\\-\sin\beta&0&\cos\beta\end{bmatrix}\begin{bmatrix}\cos\gamma&-\sin\gamma&0\\\sin\gamma&\cos\gamma&0\\0&0&1\end{bmatrix}\tag{1-2}$$

$$\text{Eqn. }(1\text{-}1)\text{ is equivalent to }R=\begin{bmatrix}r_{11}&r_{12}&r_{13}\\r_{21}&r_{22}&r_{23}\\r_{31}&r_{32}&r_{33}\end{bmatrix}\tag{1-3}$$

where:

$r_{11}=\cos\theta+x^2(1-\cos\theta)$; $r_{12}=z\sin\theta+xy(1-\cos\theta)$; $r_{13}=y\sin\theta+xz(11-\cos\theta)$;

$r_{21}=z\sin\theta+xyz(1-\cos\theta)$; $r_{22}=\cos\theta+y^2(1-\cos\theta)$; $r_{23}=x\sin\theta+yz(1-\cos\theta)$;

$r_{31}=y\sin\theta+xz(1\text{-}\cos\theta)$; $r_{32}=x\sin\theta+yz(1-\cos\theta)$; and $r_{33}=\cos\theta+z^2(1-\cos\theta)$. $\alpha$ is an angle between the x axis and the N axis, representing an amount of rotation about the z axis; $\beta$ is an angle between the z axis and the Z axis, representing an amount of rotation about the N axis; and $\gamma$ is an angle between the N axis and the X axis, representing an amount of the Z axis.

Subsequently, corresponding Euler angles can be obtained from the rotation matrix R as:

$$\theta_x=a\tan 2(r_{32},r_{33}),$$

$$\theta_y=a\tan 2\left(-r_{31},\sqrt{r_{32}^2+r_{33}^2}\right)\text{ and}$$

$$\theta_z=a\tan 2(r_{21},r_{11}),$$

where $\theta_x$, $\theta_y$和 $\theta_z$,$\theta_y$和 $\theta_z$ are angles of rotation about the x, y and z axes, respectively. From the Euler angles, the pose of the 6DoF sensor, and hence the pose of the tip section 310, can be determined.

A person of ordinary skill in the art will appreciate that when two magnetic sensors (e.g., the first magnetic sensor 341 and the second magnetic sensor 342) are held stationary and oriented at an angle relative to each other, the spatial position of each magnetic sensor can be determined. For example, a magnetic field generator may be provided at distances from the magnetic sensors, and electrical currents will be induced in the magnetic sensors by a magnetic field produced by the magnetic field generator. These currents may be fed back to position processing unit 100, which may then process the currents to determine positions of the magnetic sensors in the magnetic field and hence their positions in the space. When the two magnetic sensors are held stationary and the angle between them is kept constant, the spatial position of the tip section 310 can be determined from the spatial coordinates of the two magnetic sensors in the event of any rotation of the medical catheter. In this way, the tip section 310 can be tracked in real time. In embodiments of the present invention, the tip section 310 may include a structural member 312, and at least one of the magnetic sensors, such as the first magnetic sensor 341 may be mounted to the structural member 312.

Further, according to embodiments of the present invention, the tip section 310 may be able to deform under the action of an external force. In practice, the external force may be, for example, a contact force generated in response to the tip section 310 coming into contact with tissue in a patient's body. In this case, the medical catheter may further include a strain sensor (not shown) disposed on the tip section 310, which can measure the magnitude of a contact force exerted on the tip section 310 by tissue in the patient's body when the tip section 310 comes into contact with the tissue and responsively deforms. The strain sensor 310 may be communicatively connected to the position processing unit 100, which may be further configured to determine a vector of the contact force on the tip section 310 from the pose information of the tip section 310 and the magnitude of the contact force. Based on this force vector, the operator may assess how well the tip section 310 is fitted with the tissue in the patient's body.

In particular, referring to FIG. 3 again, the tip section 310 may include an elastomer 311, which, when deforming under the action of an external force, cause deformation of the tip section 310. The elastomer 311 may be axially connected to the structural member 312, and a proximal end of the structural member 312 may be coupled to a distal end of the bending-adjustable section 320. Alternatively, the tip section 310 may further include a tip electrode 313 connected to a distal end of the elastomer 311. The elastomer 311 may be formed of a flexible, easily deformable polymer material, which allows the elastomer 311 to deform in response to a contact force generated as a result of the tip section 310 coming into contact with tissue in the patient's body. Accordingly, the strain sensor may be mounted to the elastomer 311. The structural member 312 may be made of stainless steel or a stiff polymer material. The tip electrode 313 may be made of a platinum-iridium alloy and can be used to sense electrophysiological signals and/or for ablation.

In general, the elastomer 311 has an outer diameter which is smaller than an outer diameter of the bending-adjustable section 320. The structural member 312 can not only ensure coaxiality of the elastomer 311 and the tip electrode 313 with the bending-adjustable section 320, but can also facilitate attachment of the first magnetic positioning mechanism (e.g., both the first and second magnetic sensors may be mounted thereon, or only the first magnetic sensor may be mounted thereon, while the second magnetic sensor may be mounted on the tip electrode 313, as described in greater detail below). In addition, the stiffness of the structural member 312 enables it to provide protection to the magnetic sensor(s) mounted thereon against damage possibly caused by the tip section 310 that is being stressed.

It will be appreciated that, in case of the medical catheter being implemented as a guide sheath, the tip section 310 may not include the tip electrode 313. When the tip section 310 includes the tip electrode 313, it is endowed with mapping and/or ablation capabilities.

Figure 7:
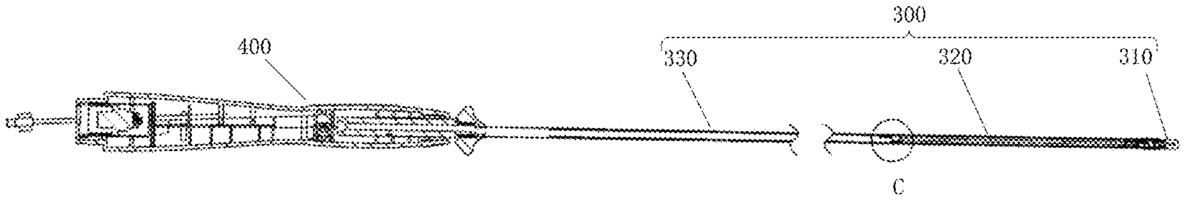
FIG. 7 is a cross-sectional view of the medical catheter in the first embodiment of the present invention.
Figure 8:
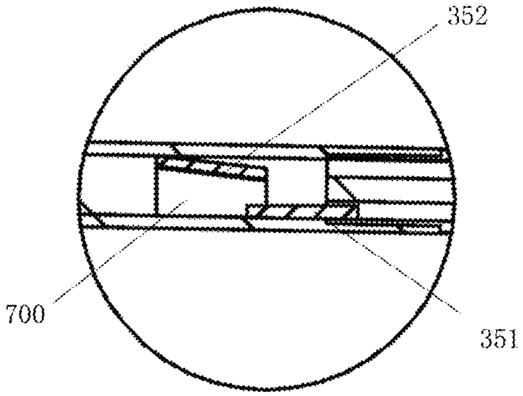
FIG. 8 is a schematic enlarged view of portion C of the medical catheter of FIG. 7.

Referring to FIGS. 7 and 8, the medical catheter may further include a second magnetic positioning mechanism disposed within the straight section 320 and located at a distal end of the straight section 330 (i.e., near the bending-adjustable section 320). It is configured to determine a pose of the distal end of the straight section 330. The second magnetic positioning mechanism includes a third magnetic sensor 351 and a fourth magnetic sensor 352. Both the third and fourth magnetic sensors 351, 352 are communicatively connected to the position processing unit 100 (possibly by the aforementioned lead 500 and connector 600). The position processing unit 100 is configured to acquire pose information of the third and fourth magnetic sensors 351, 352 and derive pose information of the distal end of the straight section 330 from the pose information of the third and fourth magnetic sensors 351, 352, as well as pose information of the bending-adjustable section 320 (about how it is bent) from the pose information of both the tip section 310 and the distal end of the straight section 330. The display unit 200 is configured to receive and display the pose information of the bending-adjustable section 320.

Like the case of the first magnetic positioning mechanism, the third and fourth magnetic sensors 351, 352 are also oriented at an angle relative to each other. The third and fourth magnetic sensors 351, 352 are preferred to be 5DoF sensors which are synthesized into a 6DoF sensor for tracking the pose of the distal end of the straight section 330. Accordingly, the position processing unit 100 is configured to generate pose information of the single 6DoF sensor from the pose information of the third and fourth magnetic sensors 351, 352 and derive the pose information of the distal end of the straight section 330 from the pose information of the 6DoF sensor.

The position processing unit is also configured to visualize the pose information of both the tip section 310 and the bending-adjustable section 320, and the display unit 200 is configured to receive and display the visualized pose information.

The structure of the medical catheter will be explained in greater detail below with reference to several preferred embodiments. In the following, all the embodiments are set forth in the context of the tip section including a tip electrode (i.e., the medical catheter having mapping and/or ablation capabilities) as an embodiment, and only differences of the medical catheter from the prior art will be described below. However, it will be appreciated that the following embodiments are not intended to limit the invention in any sense.

Embodiment 1

Referring back to FIGS. 3 to 5, 9 and 10, in this Embodiment, both the first and second magnetic sensors 341, 342 are provided on the structural member 312. Specifically, the structural member 312 defines one first channel 314 and at least one second channel 315, which are circumferentially spaced apart from one another. Moreover, an axis of the first channel 314 forms an angle with an axis of the second channel 315. Preferably, the axis of the first channel 314 forms an angle with an axis of the structural member 312, which is preferred to be 5° to 10°, while the axis of the second channel 315 is parallel to the axis of the structural member 312. The first magnetic sensor 341 is at least partially disposed in the first channel 314, and the second magnetic sensor 342 is at least partially disposed in one of the second channel(s) 315. In this way, the first and second magnetic sensors 341, 342 are oriented at an angle of 5° to 10°, and staggered along the circumferential direction of the structural member 312, with respect to each other. This can reduce mutual interference of them, resulting in higher locating accuracy. It will be appreciated that the axes of the first and second channels 314, 315 are dependent on their respective cross-sectional shapes, as explained below.

Figure 5:
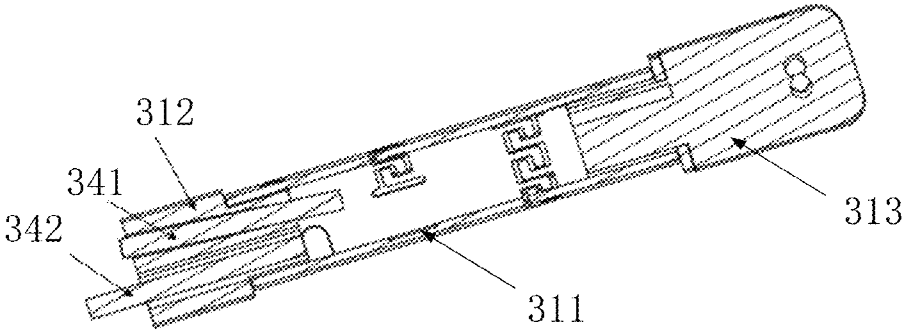
FIG. 5 is a cross-sectional view of the tip section of the medical catheter of FIG. 4 taken along B-B.

Additionally, with particular reference to FIG. 5, in this embodiment, the axis of the first channel 314 is spaced from the axis of the structural member 312 at a distance gradually decreasing from proximal to distal. Preferably, the first magnetic sensor 341 distally extends out of the first channel 314 into the elastomer 311, and the second magnetic sensor 342 proximally extends out of the second channel 315 into the bending-adjustable section 320. This is advantageous in allowing the structural member 312 to have a reduced axial length, which can mitigate interference with deformation of the tip section 310 and increase spatial utilization.

Since the tip section 310 includes the tip electrode 313, there may be three second channels 315, one of which may be configured to receive the second magnetic sensor 342 therein. Another one of the second channels 315 may be configured for passage of sensor and/or other leads (e.g., a lead of a force sensor, a lead of a temperature sensor and/or a lead of the tip electrode 313), and the remaining one of the second channels 315 may be configured to introduce a medium for cooling the tip electrode 313, such as physiological saline. It will be appreciated that the bending-adjustable section 320 may be a multi-lumen tube having lumens each corresponding to a respective one of the three second channels 315. The bending-adjustable section 320 may adopt a known prior structure, and detailed description thereof is omitted herein.

Figure 9:
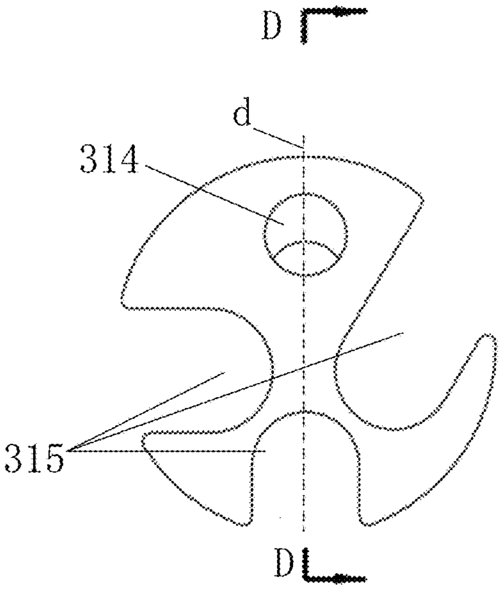
FIG. 9 is a schematic diagram showing an end face of a structural member in the medical catheter according to the first embodiment of the present invention.
Figure 10:
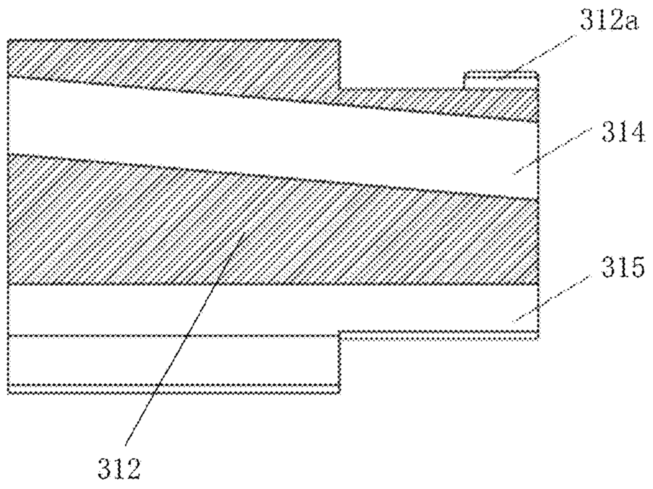
FIG. 10 is a cross-sectional view of the structural member in the medical catheter of FIG. 9 taken along D-D.

With continued reference to FIG. 9, in a radial cross-section of the structural member 312, the first channel 314 may have a circular, elliptic or other regular shape. The second channels 315 may be profiled, and may each have a contour that is at least partially open. By “open”, it is intended to mean that the contours of the second channels 315 are non-closed. A middle one of the second channels 315 opposes the first channel 314, while the remaining two second channels 315 are provided on opposing sides of the first channel 314. Moreover, the contour of each second channel 315 includes an arc edge and two straight edges extending from respective ends of the arc edge in parallel to each other. In this embodiment, the straight edges of the second channel 315 in opposition to the first channel 314 (i.e., the middle second channel 315) are parallel to a line d connecting the center of the first channel 314 and the center of the arc edge of the specific second channel 315. The straight edges of one of the second channels 315 beside the first channel 314 is perpendicular to the line d, and the straight edges of the other is inclined with respect to the line d. Moreover, the arc edge of the other is closer to the second channel 315 in opposition to the first channel 314, i.e., the distance from the center of its arc edge to the center of the arc edge of the second channel 315 in opposition to the first channel 314 is smaller than the distance from the center of its arc edge to the center of the first channel 314. For example, as shown in FIG. 9, the straight edges of the second channel 315 left to the first channel 314 are perpendicular to the line d, and the straight edges of the second channel 315 right to the first channel 314 are upwardly inclined. This configuration is adapted to improve spatial utilization of the structural member 312, maximize the angle between the first and second magnetic sensors 341, 342 for a given radial dimension of the structural member 312, and accommodate the arrangement of various leads routed in the catheter body. It is to be noted that, in this embodiment, the axes of the second channels 315 refer to straight lines passing through the centers of their respective arc edges.

In addition, in this embodiment, the third and fourth magnetic sensors 351, 352 may be arranged in any suitable manner within the distal end of the straight section 330, as long as they are oriented at a desired angle relative to each other. For example, the third magnetic sensor 351 may be attached to an inner wall of the straight section 330 so as to be parallel to an axis of the straight section 330. The fourth magnetic sensor 352 may be obliquely attached to the straight section 330 by attachment 700 in the form of an oblique groove. Alternatively, the straight section may be a double-layer tube including an inner tube defining, on its outer surface, two oblique grooves oriented at an angle with respect to each other, in which the third and fourth magnetic sensors 351, 352 are respectively accommodated.

It is to be noted that the medical catheter may further include an outer sleeve (not shown). Typically, the outer diameter of the elastomer 311 is smaller than that of the bending-adjustable section 320, and a maximum outer diameter of the structural member 312 may be equal to the outer diameter of the bending-adjustable section 320. A snap projection 312*a* at a distal end of the structural member 312 may engage a snap groove b 311*a* at a proximal end of the elastomer 311, and the outer sleeve may be fitted over the elastomer 311 and the distal end of the structural member 312, followed by application of glue therebetween for strengthening the joint between the elastomer 311 to the structural member 312. After the outer sleeve is assembled, the tip section 310 may have a smooth, neat outer surface.

Embodiment 2

Figure 11:
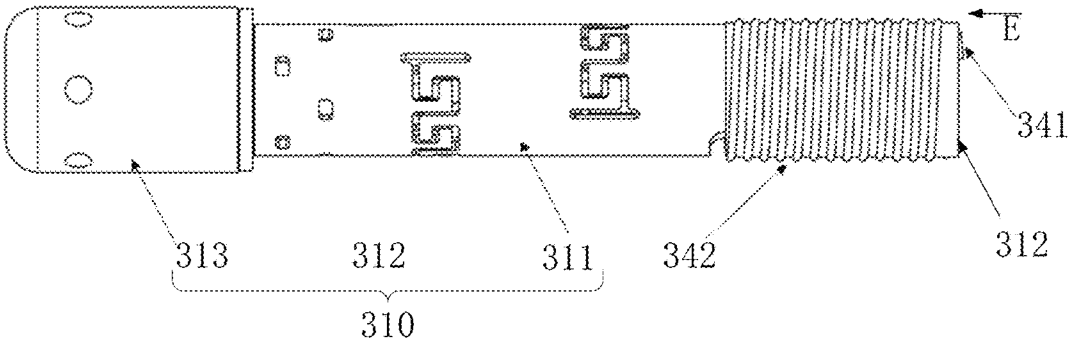
FIG. 11 is a schematic diagram showing the structure of a tip section in a medical catheter according to a second embodiment of the present invention.
Figure 12:
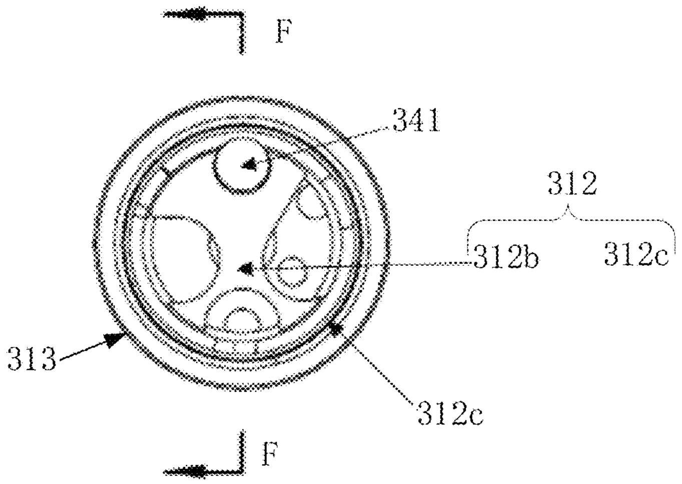
FIG. 12 is a schematic illustration of the tip section in the medical catheter of FIG. 12 as viewed in direction E.
Figure 13:
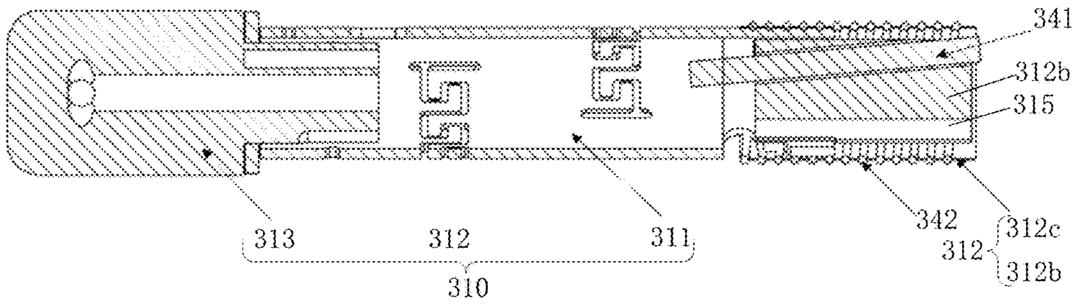
FIG. 13 is a cross-sectional view of the tip section in the medical catheter of FIG. 12 taken along F-F.

This embodiment differs from Embodiment 1 in that, as shown in FIGS. 11 to 13, the structural member 312 is configured to be ferromagnetic. The first magnetic sensor 341 is at least partially provided in the first channel of the structural member 312, and the second magnetic sensor 342 includes an inductive coil at least partially wound on an outer circumferential surface of the structural member 312. In this way, two of the three second channels 315 can be used for passage of various leads therethrough, while the remaining one may serve as a medium channel. Compared with Embodiment 1, the present embodiment is advantageous in allowing the structural member 312, which is a stiff section of the tip section 310, to have a reduced axial length, thus enabling flexible response of the catheter in the body of a patient and maximizing the (acute) angle between the first and second magnetic sensors 341, 342. Moreover, a length of the first magnetic sensor 341 that is inserted in the elastomer 311 can be adjusted to reduce interference with deformation of the tip section 310. The inductive coil may be made of an enameled wire. Alternatively, it may be made of a conductive metal and have a dielectric applied between adjacent turns.

In some implementations, the structural member 312 may be overall made of a ferromagnetic material. Alternatively, in other implementations, as shown in FIGS. 11 to 13, the structural member 312 is an assembled structure and includes a body 312*b* and a ferromagnetic core tube 312*c*. The body 312*b* is non-ferromagnetic itself and defines the first channel 314 and the second channels 315 thereon. The ferromagnetic core tube 312*c* is disposed over the body 312*b* so that the second magnetic sensor 342 is at least partially wound on an outer circumferential surface of the ferromagnetic core tube 312*c*. This design can expand the size of the second magnetic sensor to enable it to produce stronger signals, thereby imparting improved accuracy and sensitivity to the synthesized 6DoF magnetic sensor.

In this embodiment, the maximum outer diameter of the structural member 312 may be smaller than the outer diameter of the bending-adjustable section 320, and the outer sleeve may further cover the second magnetic sensor 342.

Embodiment 3

This embodiment differs from Embodiment 1 in that the first magnetic sensor 341 is provided on the structural member 312 whilst the second magnetic sensor 342 is disposed on the tip electrode 313.

Figure 14:
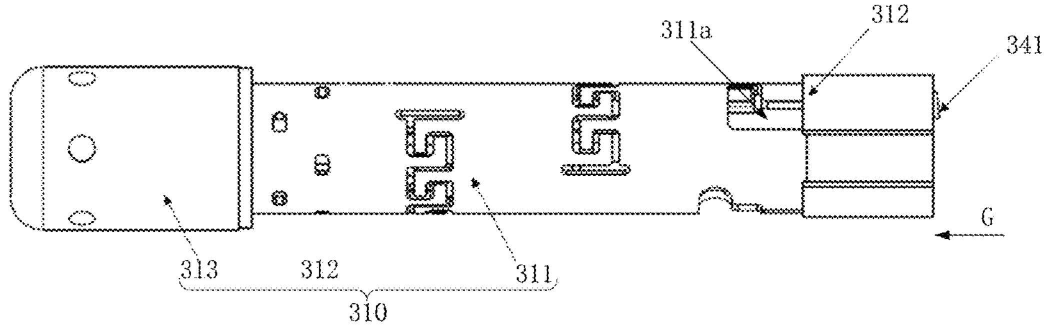
FIG. 14 is a schematic diagram showing the structure of a tip section in a medical catheter according to a third embodiment of the present invention.
Figure 15:
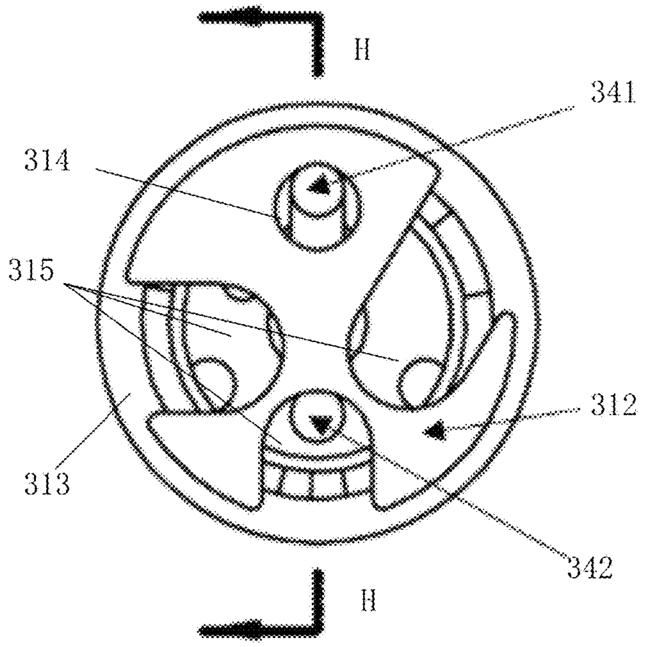
FIG. 15 is a schematic illustration of the tip section in the medical catheter of FIG. 14 as viewed in direction G.
Figure 16:
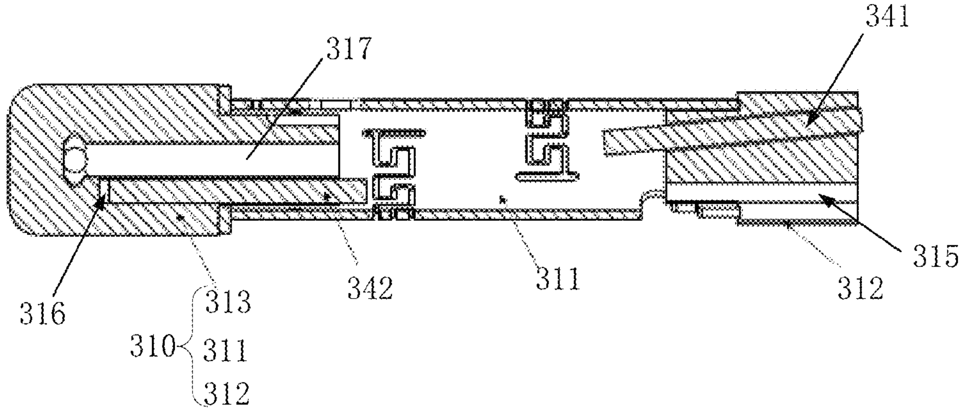
FIG. 16 is a cross-sectional view of the tip section in the medical catheter of FIG. 15 taken along H-H.

Specifically, referring to FIGS. 14 to 16, the tip electrode 313 defines a third channel 316 preferred to have an axis parallel to that of the tip electrode 313. It will be appreciated that, when the tip section 310 assumes a linear shape (i.e., before it deforms), the tip electrode 313 is coaxially with the structural member 312. At this time, the axis of the third channel 316 is parallel to the axis of the structural member 312. The second magnetic sensor 342 is at least partially disposed in the third channel 316. Preferably, a distal end of the second magnetic sensor 342 is received in the third channel 316, while its proximal end protrudes out of the third channel 316 into the elastomer 311. First, this is advantageous in that the second magnetic sensor does not occupy any space of the structural member 312 or the proximal end of the elastomer 311, allowing the two magnetic sensors to form a larger (acute) angle within the limited space. In this embodiment, the angle between the second and first magnetic sensors 342, 341 may be up to 20°, improving locating accuracy of the magnetic sensors. Second, the second magnetic sensor 342 is brought closer to a distal end of the catheter body, resulting in improved locating accuracy of the catheter tip. Third, the first and second magnetic sensors 341, 342 are axially staggered from each other, allowing them to less interfere with each other.

Preferably, on the circumference of the tip section 310, the first channel 314 is staggered from the third channel 316 (i.e., the axes of the first and third channels 314, 316 are no co-planer). This can additionally reduce mutual interference between the two magnetic sensors. The third channel 316 is aligned with one of the second channels 315, such as the middle one that opposes the first channel 314, facilitating routing of a lead of the second magnetic sensor 342 and provision of a medium passage 317 at the center of the tip electrode 313.

Although the present invention has been disclosed hereinabove, it is not limited to the above disclosure. Those skilled in the art can make various changes and modifications to the invention without departing from the spirit and scope thereof. Accordingly, it is intended that any and all such changes and modifications also fall within the scope of the present invention as defined by the appended claims and equivalents thereof.

What is claimed is:

1. A medical catheter, comprising a catheter body, a first magnetic sensor and a second magnetic sensor, the catheter body comprising, sequentially connected along an axis thereof, a tip section, a bending-adjustable section and a straight section, both the first and second magnetic sensors disposed on the tip section;

wherein the tip section comprises a structural member having a proximal end connected to the bending-adjustable section, wherein the structural member defines a first channel whose axis is at an angle with a longitudinal axis of the structural member, and the first magnetic sensor is at least partially disposed in the first channel, wherein the structural member further defines three second channels, which are circumferentially spaced apart from one another, wherein at least one of the second channels is in an angle with the first channel, and in a radial cross-section of the structural member, each of the second channels has an at least partially open contour, wherein a first one of the three second channels is configured for accommodating therein the second magnetic sensor, a second one of the three second channels is configured for passing therethrough an additional sensor and lead thereof, and a third one of the three second channels is configured for flowing therethrough a medium, wherein on a circumference of the structural member, one of the three second channels is in opposition to the first channel, and the remaining two second channels are located on opposing sides of the first channel, and wherein in the radial cross-section of the structural member, the contour of each of the second channels comprises an arc edge and two straight edges extending from respective ends of the arc edge, and wherein the straight edges of the second channel in opposition to the first channel are parallel to a line connecting a center of the first channel and a center of the arc edge of the second channel in opposition to the first channel, wherein the straight edges of one of remaining two of the second channels are perpendicular to the line, and wherein the straight edges of the other one of the remaining two of the second channels are inclined relative to the line, and a distance from a center of the arc edge of the other one of the remaining two of the second channels to the center of the arc edge of the second channel in opposition to the first channel is smaller than a distance from the center of the arc edge of the other one of the remaining two of the second channels to the center of the first channel.

2. The medical catheter according to claim 1, wherein the first and second magnetic sensors are oriented at an angle with respect to each other; wherein the angle oriented between the first and second magnetic sensors ranges from 5° to 175°.

3. The medical catheter according to claim 1, wherein an axis of each of the three second channels is configured to be parallel to the longitudinal axis of the structural member.

4. The medical catheter according to claim 1, wherein the structural member is configured to be ferromagnetic, wherein the second magnetic sensor comprises an inductive coil at least partially winding on an outer circumferential surface of the structural member, or wherein the structural member comprises a non-ferromagnetic body and a ferromagnetic core tube disposed over the body, wherein the first channel is defined in the body and the second magnetic sensor comprises an inductive coil at least partially wound on an outer circumferential surface of the structural member.

5. The medical catheter according to claim 1, wherein the angle between the axis of the first channel and the longitudinal axis of the structural member ranges from 5° to 10°.

6. The medical catheter according to claim 1, wherein the tip section further comprises an elastomer provided thereon with a strain sensor, the strain sensor configured for sensing a magnitude of an external force that the tip section is subject to when deforming.

7. The medical catheter according to claim 1, further comprising a third magnetic sensor and a fourth magnetic sensor, which are disposed within the straight section at a distal end thereof and are oriented at an angle with respect to each other; wherein the first, second, third and fourth magnetic sensors are all five-degree-of-freedom sensors.

8. A three-dimensional magnetic positioning system, comprising a positioning device and the medical catheter according to claim 1, the positioning device comprising a position processing unit and a display unit, the position processing unit communicatively connected to both the first and second magnetic sensors, the position processing unit configured to acquire pose information of both the first and second magnetic sensors and derive pose information of the tip section from the pose information of the first and second magnetic sensors, the display unit communicatively connected to the position processing unit and configured to receive and display the pose information of the tip section.

9. The three-dimensional magnetic positioning system according to claim 8, when the medical catheter further comprises the third and fourth magnetic sensors, the third and fourth magnetic sensors are disposed in the straight section at the distal end thereof and both communicatively connected to the position processing unit, wherein the position processing unit is further configured to acquire pose information of the third and fourth magnetic sensors and derive pose information of the distal end of the straight section from the pose information of the third and fourth magnetic sensors, as well as pose information of the bending-adjustable section from the pose information of both the tip section and the distal end of the straight section, and the display unit is configured to receive and display the pose information of the bending-adjustable section.

10. The three-dimensional magnetic positioning system according to claim 9, wherein the position processing unit is configured to visualize the pose information of the tip section and the pose information of the bending-adjustable section, wherein the display unit is configured to receive and display the visualized pose information, and/or, the position processing unit is further configured to derive an expected bending direction for the bending-adjustable section from the pose information of the tip section.

11. The three-dimensional magnetic positioning system according to claim 8, wherein the medical catheter further comprises a strain sensor, which is disposed on the tip section, configured to sense a magnitude of an external force acting on, and causing deformation of, the tip section, and communicatively connected to the position processing unit, wherein the position processing unit is further configured to derive a force vector on the tip section from the pose information of the tip section and the magnitude of the external force on the tip section, and the display unit is configured to receive and display the force vector.

* * * * *